United States Patent [19]

Noren et al.

[11] Patent Number: 5,385,576

[45] Date of Patent: Jan. 31, 1995

[54] METHOD FOR DETECTING VENTRICULAR FIBRILLATION AND APPARATUS FOR DETECTING AND TREATING VENTRICULAR FIBRILLATION

[75] Inventors: Kjell Noren, Solna; Pia Hagel, Sollentuna; Kurt Hoegnelid, Voesterhuninge, all of Sweden

[73] Assignee: Siemens Atiengesellschaft, Munich, Germany

[21] Appl. No.: 101,727

[22] Filed: Aug. 4, 1993

[30] Foreign Application Priority Data

Aug. 18, 1992 [EP] European Pat. Off. ........... 92114090

[51] Int. Cl.⁶ ................................................ A61N 1/39
[52] U.S. Cl. ....................................... 607/6; 128/734; 128/705
[58] Field of Search ............... 128/705, 713, 706, 734; 607/5, 6, 8

[56] References Cited

U.S. PATENT DOCUMENTS 4,674,518 6/1987 Salo ..................................... 128/734
4,697,591 10/1987 Lekholm et al. .
5,058,583 10/1991 Geddes et al. .

FOREIGN PATENT DOCUMENTS 0009255 4/1980 European Pat. Off. .
0074126 3/1983 European Pat. Off. .
2070282 9/1981 United Kingdom .

*Primary Examiner*—William E. Kamm
*Assistant Examiner*—Kennedy J. Schaetzle
*Attorney, Agent, or Firm*—Hill, Steadman & Simpson

[57] ABSTRACT

In a method and apparatus for detecting ventricular fibrillation, a measured impedance signal, dependent on the blood volume in the heart, is evaluated, and ventricular fibrillation is assumed to be present if the level of the measured impedance signal falls below a predetermined threshold. This is based on the perception that as the heart fills with blood, given the presence of ventricular fibrillation, the level of the measured impedance signal will decrease. The apparatus also includes circuitry for treating the detected ventricular fibrillation.

11 Claims, 2 Drawing Sheets

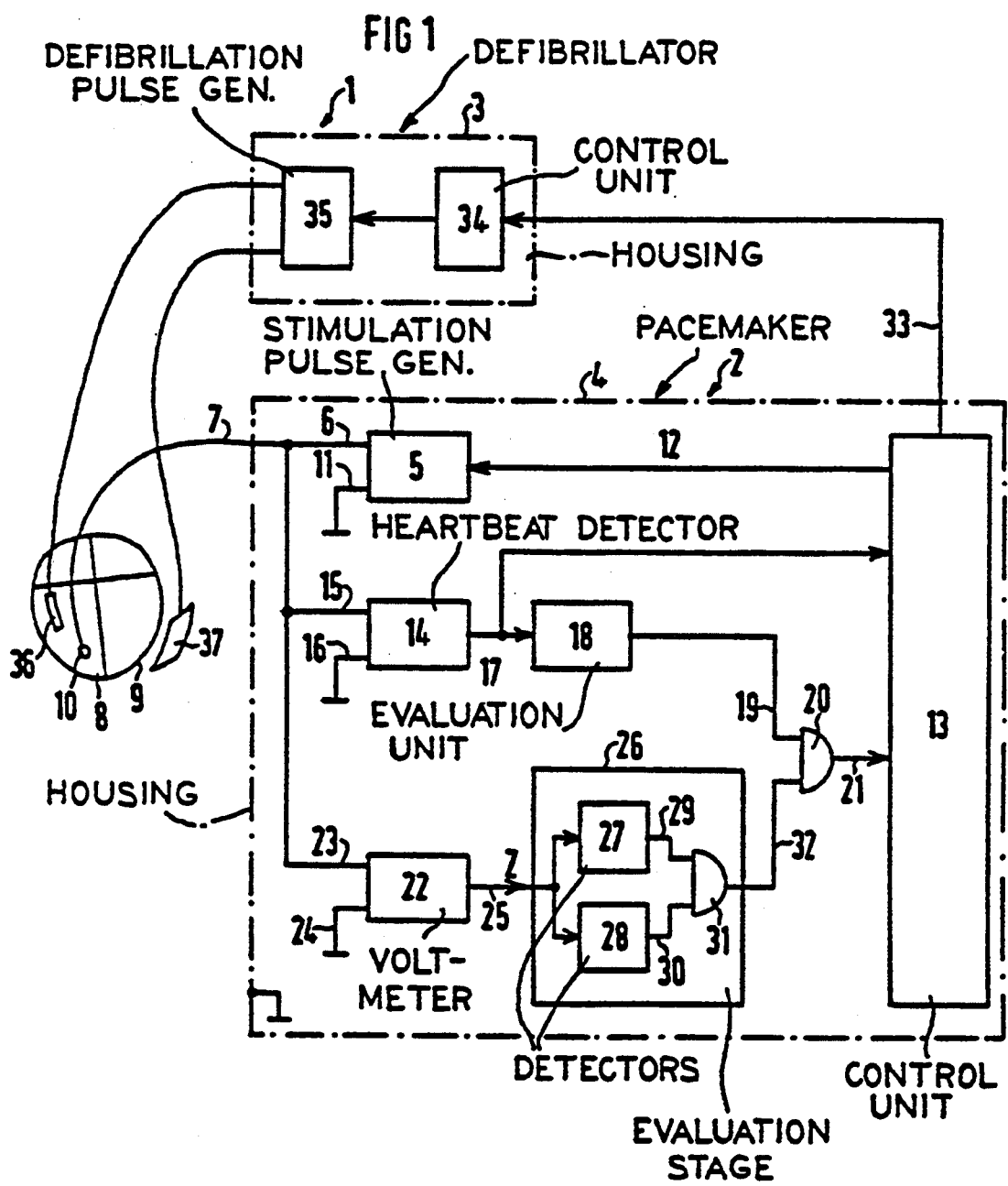

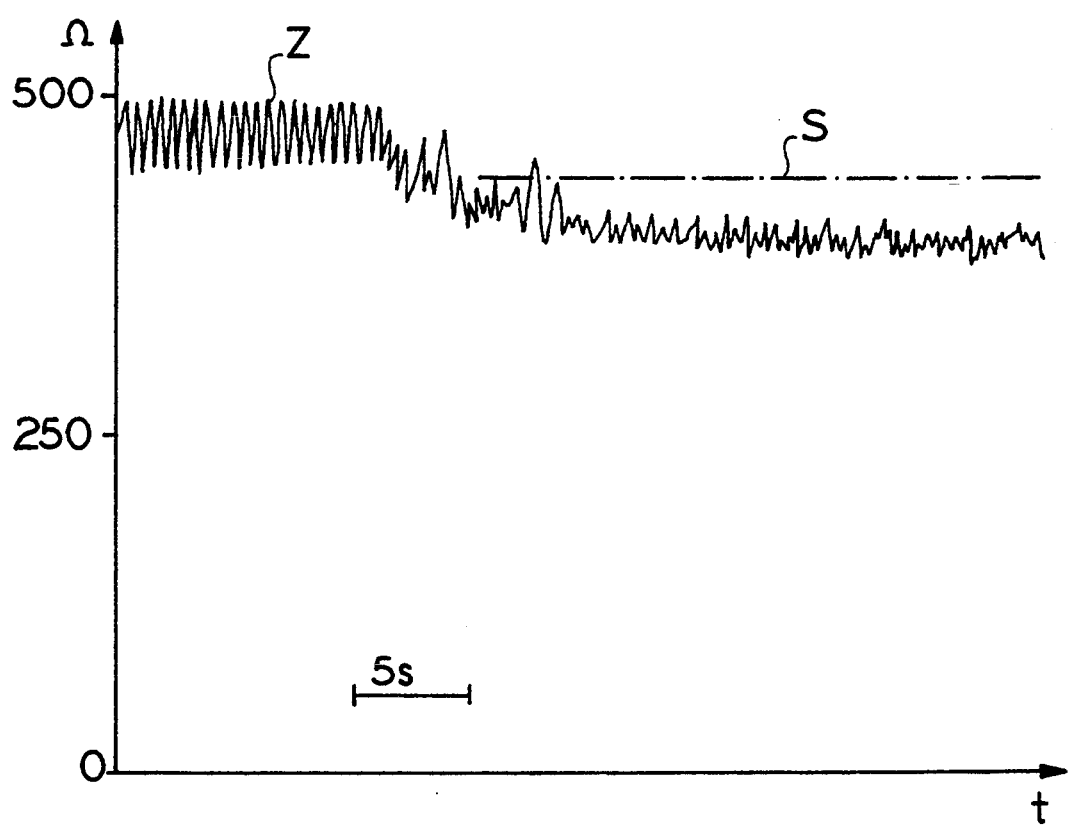

METHOD FOR DETECTING VENTRICULAR FIBRILLATION AND APPARATUS FOR DETECTING AND TREATING VENTRICULAR FIBRILLATION

BACKGROUND OF THE INVENTION

1. Field of the Invention

The present invention is directed to a method for detecting ventricular fibrillation by evaluating a measured impedance signal dependent on the blood volume in the heart, as well as to an apparatus for detecting and treating ventricular fibrillation.

2. Description of the Prior Art

Ventricular fibrillation is one of a number of rhythm disturbances of the heart exhibiting an unnaturally elevated frequency (contraction repetition rate) caused by pathologies of the heart's natural pacemaker, or pathologies arising in the conductive paths within the heart. Such rhythm disturbances are generically referred to as tachyarrhythmia, and result in a reduced ventricular filling and a reduced ejection power of the heart. In the worse case, i.e., ventricular fibrillation, the disturbances can result in a standstill of the blood conveying capability of the heart. In order to be able to administer a therapy technique best suited for treating the particular types of tachyarrhythmia, such as antitachycardiac stimulation, cardioversion or defibrillation, a recognition of the particular rhythm disturbance of the heart is first required. The detection of tachyarrhythmia only with the assistance of an intracardial electrogram and subsequent evaluation of criteria related to heartbeat rate, such as frequency, sudden frequency increase, or a persisting, high-frequency value, can thus be problematical.

In general, it is known to obtain a measured impedance signal which is dependent on the blood volume in the heart, and to evaluate the measured impedance signal to obtain information about the current condition of the heart. It is also known to activate and control pulse generating means for delivering electrical stimulation pulses to the heart based on the result of the evaluation of the impedance signal.

European Application 0 009 255 discloses the detection of ventricular fibrillation by evaluating both electrical and mechanical activity of the heart. Defibrillation of the heart is then triggered following the detection ventricular fibrillation. For acquiring signals corresponding to the electrical activity of the heart, the intracardial electrogram is obtained from the heart with an electrode arrangement. The mechanical activity of the heart is identified by obtaining a measured impedance signal, which dependent on the blood volume in the heart, using the same electrode arrangement, having an impedance measuring means connected thereto. Changes in the measured impedance signal which are dependent on the contractions of the heart are then evaluated.

In order to be able to identify the changes of the measured impedance signal which are dependent on the contractions of the heart in this known system, a plurality of individual measured values must be acquired and evaluated. The number of measured values required for this purpose is high in comparison to the contraction rate of the heart.

SUMMARY OF THE INVENTION

It is an object of the present invention to provide a reliable method and apparatus for the detection of ventricular fibrillation, with a minimum of measurement outlay.

It is also an object of the present invention to provide an apparatus for treating ventricular fibrillation in response to a detection thereof by such a method.

The above objects are achieved in accordance with the principles of the present invention in a method for detecting ventricular fibrillation wherein the measured impedance signal is evaluated, and a drop of the level of the measured impedance signal below a predetermined threshold is utilized as a criteria for indicating the presence of ventricular fibrillation.

The above objects are achieved in an apparatus constructed in accordance with the principles of the present invention having an evaluation means in the form of a detector means for detecting a drop in the level of the measured impedance signal below a predetermined threshold. The apparatus also includes circuitry for treating the detected ventricular fibrillation.

The method and apparatus are both based on the perception that, as the heart fills with blood given the presence of ventricular fibrillation, the general impedance level decreases. By acquiring the level of the measured impedance signal, one can thereby reliably detect ventricular fibrillation, and can also distinguish it from other types of tachyarrhythmia. Moreover, the level of the measured impedance signal, in terms of measuring techniques and hardware components, is especially easily acquired, because only a very few measured values are required to obtain a useable detection result, in comparison to the aforementioned acquisition and evaluation of the changes of the measured impedance signal.

In order to preclude the influence of longer-lasting fluctuations of the level of the measured impedance signal on the detection of ventricular fibrillation, preferably a chronological average of the level of the measured impedance signal is calculated. The average is calculated for a time during normal functioning of the heart, and the threshold is then set to a value which lies below this "normal" average by a prescribed amount. Correspondingly, the evaluation means in the apparatus of the invention includes an averaging unit for formulating a running chronological average of the level of the measured impedance signal, and for setting the threshold to a value which lies below the "normal" average by a prescribed amount.

The reliability with which the presence of ventricular fibrillation is detected can be enhanced by using the speed with which the level of the measured impedance signal drops as a further criterion for identifying the presence of ventricular fibrillation. In a corresponding embodiment of the apparatus of the invention, the evaluation means includes further detector means for detecting the speed with which the level of the measured impedance signal drops, and means for logically operating on the output signals generated by the detector means and by the further detector means, such that the simultaneous presence of both output signals indicates ventricular fibrillation. The means for logically operating on the output signals can be an AND element, or it can be provided that one of the two detector means is activated by the output signal of the other detector means in a sequence.

For further enhancing the detection reliability, the contraction repetition rate is preferably also acquired and evaluated as an additional criterion for identifying the presence of ventricular fibrillation. To this end, a heartbeat detector is provided in the apparatus of the invention, which is followed by a further evaluation means for identifying the heartbeat rate, and the output signals of the impedance signal evaluation means and the heartbeat rate evaluation means are then logically combined with each other, such that the simultaneous presence of both output signals indicates ventricular fibrillation.

The measuring of the level of the impedance signal ensues in a particularly simple manner in an embodiment wherein the impedance measuring means comprises means for identifying the measured impedance signal from electrical pulses supplied to the heart by the pulse-generating unit of the apparatus, via the same electrode arrangement which is used to deliver the stimulation pulses. If it is desired that the electrical pulses used for the purpose of conducting the impedance measurement not result in a stimulation of the heart, the electrical pulses generated for identifying the measured impedance signal can have a pulse amplitude which lies below the stimulation threshold of the heart. In the simplest case, the pulse-generating unit is composed of a defibrillation pulse generator operable in a measurement mode to generate pulses having the lowest possible energy for identifying the measured impedance signal, and in a therapy mode for delivering high-energy pulses upon the detection of ventricular fibrillation.

In an alternative embodiment of the apparatus of the invention, the pulse-generating unit includes a stimulation pulse generator for delivering cardiac pacing pulses, and a separate defibrillation pulse generator, activatable by the impedance signal evaluation means, for delivering defibrillation pulses. The electrical pulses generated by the stimulation pulse generator are supplied to the means for identifying the measured impedance signal from the electrical pulses. Although the evaluation of pacemaker pulses for acquiring a respiration-dependent measured impedance signal is described in U.S. Pat. No. 4,697,591, the method and apparatus of the invention permit the application of this measurement principle and the advantages connected therewith for the first time to the detection of ventricular fibrillation, by means of impedance measurement dependent on the blood content of the heart. Moreover, in the known method described in the earlier-cited European Application 0 009 255, wherein heart pacemaker pulses are used to identify the measured impedance signal, substantially more measured values are required for the evaluation of the changes of the measured impedance signal dependent on the pumping activity of the heart than are needed in the method and apparatus disclosed herein.

DESCRIPTION OF THE DRAWINGS

FIG. 1 is schematic block diagram of an apparatus for detecting and treating ventricular fibrillation constructed in accordance with the principles of the present invention, and operating for the detection of ventricular fibrillation according to the method of the invention.

FIG. 2 shows an example of a curve of a measured impedance signal dependent on the blood volume in the heart for use in accordance with the principles of the present invention, given normal cardiac activity and given the presence of ventricular fibrillation.

DESCRIPTION OF THE PREFERRED EMBODIMENTS

FIG. 1 shows a block circuit diagram of a combined defibrillator 1 and heart pacemaker 2 constructed in accordance with the principles of the present invention. Both devices are capable of being arranged in a common, implantable housing or, as shown in FIG. 1, the devices can be respectively arranged in implantable housings 3 and 4.

The heart pacemaker 2 contains a stimulation pulse generator 5 having an out terminal 6 connected via an electrode line 7 to a stimulation electrode 10 arranged in the ventricle 8 of a heart 9. The second output terminal 11 of the stimulation pulse generator 5 is connected to the housing 4 of the heart pacemaker 2, which serves as the return electrode for the stimulation electrode 10. The stimulation pulse generator 5 is connected via a control line 12 to a pacemaker control 13, which initiates the output of stimulation pulses by the stimulation pulse generator 5 via the control line 12. A heartbeat detector 14, for detecting stimulated or natural cardiac activities, has a first input terminal 15 connected to the stimulation electrode 10, and has a second input terminal 16 connected to the housing 4 of the pacemaker 2. For controlling the function of the pacemaker 2 dependent on the detected electrical heart activities, the heartbeat detector 14 has an output 17 connected to the heart pacemaker control unit 13. An evaluation unit 18, which evaluates the detected electrical heart activities with respect to their frequency (repetition rate) is also connected to the output 17 of the heartbeat detector 14. The evaluation unit 18 has output connected to a first input 19 of an AND element 20, which has an output 21 connected to the pacemaker control unit 13.

A voltmeter 22 is also contained in the housing 4 of the pacemaker 2, and has a first input terminal 23 connected to the stimulation electrode 10 and a second input terminal 24 connected to the housing 4. The voltmeter 22, in combination with the pulse generator 5, form an impedance measuring means wherein the drop of the pulse amplitude of the stimulation pulses generated by the stimulation pulse generator 5 between the start of each stimulation pulse and the end of that stimulation pulse is identified. The output of the voltmeter 22 thus constitutes a transcardial measured impedance signal Z, derived from the aforementioned drop in the pulse amplitude. The measured impedance signal Z is supplied from the output 25 of the voltmeter 22 to an input of an evaluation stage 26. The evaluation stage 26 includes a first detector 27 for detecting the drop in the level of the measured impedance signal Z below a predetermined threshold, and a second detector 28 wherein the speed with which the level of the measured impedance signal Z changes is monitored to determine whether the speed of the change upwardly transgresses a minimum speed. The two detector 27 and 28 have respective outputs 29 and 30 connected through an AND element 31 to a second input 32 of the AND element 20.

The pacemaker control unit 13 is thus informed via the output 31 of the AND element 20 of the presence of ventricular fibrillation when the contraction repetition rate upwardly exceeds a prescribed value and when the level of the transcardiac impedance falls below a prescribed threshold with a minimum speed, for example, within a prescribed time window.

In response, the pacemaker control unit 13 generates a control signal to a control unit 34 of the defibrillator 1 via a control line 33. Alternatively, the pacemaker control unit 13 can communicate with the control unit 34 via a wireless signal transmission link. The control unit 34 thereupon activates a defibrillation pulse generator 35 to cause the delivery of a defibrillation pulse to the heart 9 via two defibrillation electrodes 36 and 37.

An example of the curve of the measured impedance signal Z acquired between the stimulation electrode 10 and the housing 4 of the pacemaker 2 is shown in FIG. 2, given natural heart activity and given ventricular fibrillation thereafter. As shown in FIG. 2, the measured impedance signal Z during the natural heart activity varies dependent on the contractions of the heart muscle. Upon the appearance of ventricular fibrillation, the pumping activity of the heart changes to a high-frequency, uncoordinated twitching of the myocardium, for which reason the frequency of the changes of the measured impedance signal Z increases, and the amplitude of the changes of the impedance signal Z drops. These phenomena are used in the aforementioned European Application 0 009 255 for evaluating the mechanical activity of the heart. As shown in FIG. 2, however, the general level of the measured impedance signal Z suddenly drops given the appearance of ventricular fibrillation. This is attributed to the fact that the heart muscle is no longer pumping the blood given ventricular fibrillation, but is instead filling with blood. Given the apparatus shown in FIG. 1, this effect is utilized by detecting the sudden drop in the level of the measured impedance signal Z below the prescribed threshold S, this drop being a criterion for indicating the presence of ventricular fibrillation. It is sufficient for identifying the level of the measured impedance signal Z to acquire the measured values of the transcardial impedance with a low sampling frequency corresponding, for example, to the stimulation rate of the stimulation pulse generator 5 in FIG. 1. A running average is formed over a few, for example, five, of the acquired measured values in order to suppress the influence of noise-like changes of the measured impedance signal Z on the detection of a downward transgression of the threshold S. It can also be provided, instead of this short-term averaging, to use a defined plurality of successive measured values which have downwardly transgressed the threshold S, in order to detect a drop in the level of the impedance signal Z below the threshold S.

In order to be able to adapt the threshold S to longer-lasting fluctuations or changes of the impedance level, a long-term average is additionally formed in the evaluation unit 26 from the measured values of measured impedance signal Z, and the threshold S is set to a value below the normal the average by a prescribed amount.

Alternatively to the exemplary embodiment of the apparatus shown in FIG. 1, low-energy electrical pulses generated by the defibrillation pulse generator 35 can be used instead of the pacemaker pulse generated by the stimulation pulse generator 5 for measuring the transcardial impedance. In this case, the voltmeter 22 is then connected to one or both of the defibrillation electrodes 36 and 37. As a further alternative, an impedance measuring means which is independent of both the pulse generators 5 and 35 can be used.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for detecting ventricular fibrillation comprising the steps of:
    evaluating a measured impedance signal obtained from a heart, dependent on blood volume in said heart; and
    identifying the occurrence of a drop in the level of said measured impedance signal below a prescribed threshold as indicating the presence of ventricular fibrillation.

2. A method as claimed in claim 1 comprising the additional step of:
    forming a chronological average of said level of said measured impedance signal; and
    setting said threshold at a value below said average by a predetermined amount.

3. A method as claimed in claim 1 comprising the additional steps of:
    monitoring the speed at which said level of said measured impedance signal drops; and
    using said speed at which said level of said measured impedance signal drops as a further indication of the presence of ventricular fibrillation.

4. A method as claimed in claim 1 comprising the additional steps of:
    monitoring the heartbeat rate of said heart; and
    using said heartbeat rate as an additional indication of the presence of ventricular fibrillation.

5. An apparatus for detecting and treating ventricular fibrillation comprising:
    impedance measuring means for acquiring a measured impedance signal from a heart, dependent on the blood volume in said heart;
    evaluation means connected to said impedance measuring means for evaluating said measured impedance signal and for detecting a drop in the level of said measured impedance signal below a predetermined threshold, said drop being indicative of the presence of ventricular fibrillation;
    pulse generator means, activatable by said evaluation means, for generating electrical pulses; and
    electrode means, connected to said pulse generator means, for delivering said electrical pulses to said heart.

6. An apparatus as claimed in claim 5 wherein said evaluation means further includes averaging means for formulating a running chronological average of said level of said measured impedance signal and for setting said threshold to a value below said average by a predetermined amount.

7. An apparatus as claimed in claim 5 wherein said evaluation means includes further detector means for detecting the speed with which said level of said measured impedance signal drops, and means for logically combining output signals from said detector means and said further detector means for indicating the presence of ventricular fibrillation given the simultaneous presence of an output signal from said detector means and from said further detector means.

8. An apparatus as claimed in claim 5 further comprising:
    means for detecting heartbeats of said heart;
    further evaluation means for identifying a heartbeat rate from said heartbeats; and means for logically combining outputs of said evaluation means and said further evaluation means for indicating the presence of ventricular fibrillation given the simultaneous presence of an output from said evaluation means and from said further evaluation means.

9. An apparatus as claimed in claim 5 wherein said impedance measuring means comprises means for identifying said measured impedance signal from said electrical pulses generated by said pulse generator means and delivered to said heart via said electrode means.

10. An apparatus as claimed in claim 9 wherein said pulse generator means comprises means for generating pulses for identifying said measured impedance signal having a pulse amplitude below a stimulation threshold of said heart.

11. An apparatus as claimed in claim 9 wherein said pulse generator means comprises a stimulation pulse generator for generating pacemaker pulses and defibrillation pulse generator, activatable by said evaluation means, for generating defibrillation pulses, and wherein said electrical pulses generated by said stimulation pulse generator are supplied to said impedance measuring means.

* * * * *